(12) United States Patent
Nelson et al.

(10) Patent No.: US 11,590,433 B2
(45) Date of Patent: Feb. 28, 2023

(54) RAPID SOLID PHASE EXTRACTION DEVICE AND METHODS

(71) Applicant: Tetracore, Inc., Rockville, MD (US)

(72) Inventors: William M. Nelson, Rockville, MD (US); Kyle Armantrout, Los Angeles, CA (US); David R. Almassian, Gaithersburg, MD (US); Aymeric Randanne de Vazeille, Leesburg, VA (US); Tracy Calvin Fecteau, Ellicott City, MD (US); Colin Kuserk, Derwood, MD (US)

(73) Assignee: Tetracore, Inc., Rockville, MD (US)

( * ) Notice: Subject to any disclaimer, the term of this patent is extended or adjusted under 35 U.S.C. 154(b) by 450 days.

(21) Appl. No.: 16/698,211

(22) Filed: Nov. 27, 2019

(65) Prior Publication Data

US 2020/0094165 A1 Mar. 26, 2020

Related U.S. Application Data

(62) Division of application No. 15/235,959, filed on Aug. 12, 2016, now Pat. No. 10,525,375.

(60) Provisional application No. 62/205,266, filed on Aug. 14, 2015.

(51) Int. Cl.
| | |
|---|---|
| *B01D 15/14* | (2006.01) |
| *B01D 15/42* | (2006.01) |
| *B01D 15/22* | (2006.01) |
| *B01D 15/02* | (2006.01) |
| *B01D 15/20* | (2006.01) |
| *B01D 15/34* | (2006.01) |
| *B01D 15/18* | (2006.01) |
| *C12N 15/10* | (2006.01) |

(52) U.S. Cl.
CPC ............. *B01D 15/14* (2013.01); *B01D 15/02* (2013.01); *B01D 15/1871* (2013.01); *B01D 15/20* (2013.01); *B01D 15/22* (2013.01); *B01D 15/34* (2013.01); *B01D 15/426* (2013.01); *C12N 15/1006* (2013.01)

(58) Field of Classification Search
CPC .... B01D 15/14; B01D 15/02; B01D 15/1871; B01D 15/20; B01D 15/22; B01D 15/34; B01D 15/426; C12N 15/1006
See application file for complete search history.

(56) References Cited

U.S. PATENT DOCUMENTS

| | | | | |
|---|---|---|---|---|
| 5,691,206 | A * | 11/1997 | Pawliszyn | B82Y 30/00 73/61.76 |
| 6,770,246 | B1 * | 8/2004 | Husek | B01L 3/0275 436/178 |
| 7,837,871 | B2 * | 11/2010 | Gjerde | B01L 3/0275 210/100 |
| 2006/0118491 | A1 * | 6/2006 | Gjerde | G01N 30/6091 435/7.1 |

(Continued)

FOREIGN PATENT DOCUMENTS

CN 102357312 B * 10/2013

*Primary Examiner* — Emmanuel E Duke
(74) *Attorney, Agent, or Firm* — Finnegan, Henderson, Farabow, Garrett & Dunner, LLP

(57) ABSTRACT

A method and system for solid phase extraction of a compound of interest from a sample matrix using a syringe having a barrel and a plunger, a sorbent for use with the syringe, and a desalting purification column having an end configured to receive liquid from the syringe body.

20 Claims, 7 Drawing Sheets

(56) References Cited

U.S. PATENT DOCUMENTS

2011/0042317 A1* 2/2011 Gjerde .................. G01N 35/10
                                                                   210/656
2016/0159856 A1   6/2016 Baaneyx et al.

* cited by examiner

RAPID SOLID PHASE EXTRACTION DEVICE AND METHODS

PRIORITY CLAIM

This application is a divisional of U.S. patent application Ser. No. 15/235,959, filed Aug. 12, 2016, which claims priority from U.S. Provisional Patent Application No. 62/205,266 filed on Aug. 14, 2015, which are hereby incorporated by reference in their entireties in the present application.

BACKGROUND

Technical Field

The present disclosure relates to solid phase extraction techniques of molecules of interest, and apparatus for achieving these techniques. The techniques of the present disclosure eliminate the need for centrifugation of samples standard in conventional solid phase extraction. The techniques of the present disclosure also eliminate the need for specialized laboratory skills and equipment (e.g. micropipettes).

More specifically, the present disclosure relates to apparatus for passing a volume of sample using a syringe device through sorbent to bind a substance of interest and subsequently eluting the substance of interest from the sorbent using the syringe device without the need for centrifugation. In illustrative embodiments, examples of sorbents for isolating nucleic acids as the substance of interest include, but are not limited to: silica, acid washed silica, glass beads, acid washed glass beads, zeolite, silica gel, filters embedded with silica particles, or mixtures of the above.

Description of Related Art

Solid phase extraction (SPE) is a useful sample preparation technique for isolating or purifying compounds of interest from a liquid sample matrix. SPE relies on physical properties of compounds of interest to capture them from the sample matrix. For example, SPE is used to isolate DNA from cells lysate, whole blood, serum, plasma, sputum, urine, fecal, semen, cerebro-spinal fluid or oral fluids. SPE is an efficient process, and advantageously avoids problems common in other liquid/liquid extraction techniques such as incomplete phase separations, specialty glassware and the need to use and dispose large quantities of organic solvents.

SPE samples are frequently prepared for downstream use in polymerase chain reaction (PCR), where contaminants or other molecules not of interest to the analysis could inhibit the PCR. Other molecular diagnostic testing modalities exist, such as NASBA, RPA, HDA, LAMP, RCA, ICAN, SMART, SDA, microarray, and LDR. All molecular diagnostic testing modalities benefit from a stronger signal through sample isolate purity. The purities achievable using SPE render it an attractive tool for molecular diagnostics for public health laboratories, biotechnology companies, government agencies, law enforcement agencies, and research institutes.

There are numerous technique variations for using SPE, which vary by how compounds are retained by a substance known as the sorbent. Variants include reversed-phase, normal-phase, ion-exchange and adsorption. A common approach that uses a silica sorbent membrane is the spin column procedure known as QIAamp available from Qiagen N.V., Venlo, The Netherlands, used for instance for nucleic acid purification from tissues, swabs or body fluids (e.g., blood, sweat, washed urine cells, semen, cerebro-spinal fluid, etc.). In this procedure, depicted in FIG. 1 and discussed in greater detail below, samples are lysed, binded to the silica membrane and washed. The purified nucleic acid is then eluted from the silica membrane.

Unfortunately, the prior art approach for sample extraction involves either the use of micropipettes and centrifuges to process the sample at each stage. Further, the volume of the sample in traditional extraction is typically limited, for example to 140 µl, and greater volumes require additional centrifugations. Traditional silica column based extractions (such as Qiagen, QIAamp Viral RNA, catalog 52904), require that the sample with lysis buffer and alcohol is loaded into the spin column. Based on the size of the spin column, only 630 µL can typically be loaded at one time. A 140 µL sample requires 560 µL of lysis buffer and 560 µL of ethanol, which requires two centrifugation spins to load all of the sample/buffer through the silica.

SUMMARY

The present disclosure includes techniques and apparatus for preparing purified compounds of interest using various SPE principles including sorbent extraction, embodied in a syringe-based system, eliminating the need for a laboratory centrifuge or pipettes.

In certain embodiments, PCR inhibitors are rapidly removed from clinical samples to create a PCR-ready sample. The method may in an illustrative embodiment comprise the preparation of a polynucleotide-containing sample that is substantially free of inhibitors.

According to exemplary embodiments, a larger volume of sample can be processed in a single iteration of sample preparation according to the present disclosure as compared with traditional SPE methods.

Advantageously, by eliminating the need for time-consuming centrifugation the efficiency of the molecular diagnostic process is increased. Further, the removal of the centrifuge in the disclosed process permits performance of SPE of compounds of interest away from the laboratory, permitting accurate and sensitive molecular diagnostics to be performed alongside portable molecular diagnostics analyzers in hospitals, emergency scenes, battlefields, athletic fields, crime scenes, remote research locations, etc.

Advantageously, specialized laboratory skills and equipment (e.g. micropipettes) are not required to operate the invention, allowing the invention to be used at the point-of-care by a minimally trained operator.

According to one embodiment, a method is disclosed for extracting a compound of interest from a sample matrix, comprising the steps of drawing a sample matrix into a syringe having a plunger containing a premixed lysis buffer solution; allowing the sample matrix and lysis buffer to incubate for a suitable period of time; expelling the sample mixed with lysis buffer through a sorbent membrane to bind the compound of interest to the sorbent; drawing elution buffer into the syringe containing the sorbent membrane; optionally allowing the sorbent membrane and elution buffer containing the compound of interest to incubate for a suitable period of time; expressing the elution buffer containing the compound of interest through a desalting column using the syringe plunger.

According a further embodiment, a system for solid phase extraction of a compound of interest from a sample matrix is disclosed comprising a syringe, the syringe further having a barrel and a plunger, the barrel comprising a hub with an opening at a first end and a sorbent membrane on the interior of the barrel proximate to the hub; a desalting purification column comprising a barrel having a connector end for attaching to the syringe, and an exit end, and further having a desalting chamber fluidly connecting said connector end and said exit end; wherein the connector end of the desalting purification column and the hub of the syringe are configured for selectably mating to one another.

In an exemplary embodiment, a sorbent need not be a sorbent membrane. Examples of sorbents include, but are not limited to, silica, acid washed silica, glass beads, acid washed glass beads, zeolite, silica gel, filters embedded with silica particles, or mixtures of the above.

In an exemplary embodiment, sorbent beads can be retained between two filters. In an exemplary embodiment, filters for retaining sorbent may be made from poylpropylene.

In an exemplary embodiment, sorbent beads may be retained by a filter only at the first end of the syringe, thereby allowing the sorbent beads to float freely in the sample matrix and/or buffers. In an exemplary embodiment, filters for retaining sorbent may be made from poylpropylene.

According to another embodiment, a method is disclosed for extracting a compound of interest from a sample matrix, comprising the steps of drawing a sample matrix into a syringe; drawing one or more buffer solutions, either sequentially or premixed, into the syringe (where one or more buffers may be a lysis buffer); allowing the sample matrix and lysis buffer to incubate for a suitable period of time; attaching a sorbent cartridge to the syringe; expelling the sample mixed with buffers through the sorbent cartridge to bind the compound of interest to the sorbent; optionally drawing wash buffers through the sorbent cartridge into the syringe and expelling them through the sorbent cartridge; drawing elution buffer through the sorbent cartridge and into the syringe; optionally allowing the sorbent and elution buffer containing the compound of interest to incubate for a suitable period of time; expressing the elution buffer containing the compound of interest through the sorbent cartridge and into a desalting column; allowing the elution buffer containing the compound of interest to gravity drip through the desalting column.

According a further embodiment, a system for solid phase extraction of a compound of interest from a sample matrix is disclosed comprising a syringe, the syringe further having a barrel and a plunger, the barrel comprising a hub with an opening that has a luer lock fitting at a first end; a sorbent cartridge comprising a barrel having a connector end for attaching to the syringe; a desalting purification column comprising a barrel having an exit end, and further having a desalting chamber fluidly connecting said barrel and said exit end; wherein the exit end of the desalting purification column is positioned in a rack for gravity dripping directly into a reaction cartridge, reaction tube, or collection tube.

According to a further embodiment, the desalting purification column may be omitted.

According a further embodiment, the elution buffer is pushed or pulled through the desalting column as opposed to gravity drip.

BRIEF DESCRIPTION OF DRAWING(S)

The invention and the following detailed description of certain embodiments thereof may be understood by reference to the following figures.

DETAILED DESCRIPTION

Figure 1:
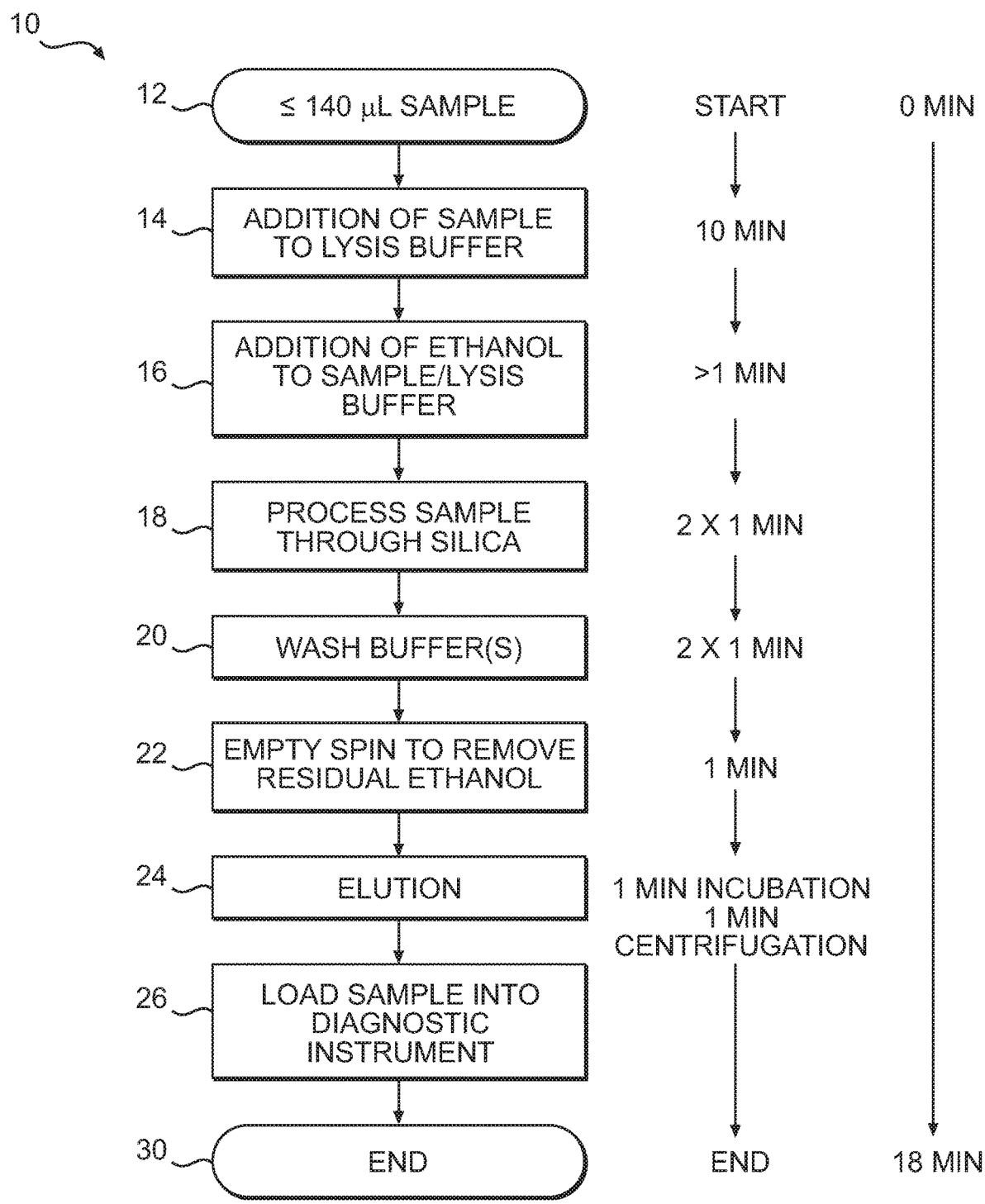
FIG. 1 illustrates a prior art method for solid phase extraction of a compound of interest from a sample matrix.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation. Moreover, it is to be appreciated that the drawings may not be to scale. Moreover, the word "exemplary" is used herein to mean serving as an example, instance, or illustration. Any aspect or design described herein as "exemplary" is not necessarily to be construed as preferred or advantageous over other aspects or designs.

Other exemplary substances of interest include various proteins as well as nucleic acids, and fragments thereof. With the proper selection of sorbent, SPE can be used to isolate other substances of interest such as contaminants, aromatic compounds, phenols, nitroaromatics, pesticides heavy metals, preservatives and dyes, as well as drugs, antibiotics, vitamins, fatty acids, trace elements, lipids, steroids, carbohydrates, etc. The devices, systems and methods according to the present disclosure can be used to isolate substances of interest from a variety of matrices, including urine, whole blood, serum, plasma, sputum, oral fluids, water, food and beverages, soil, waste oil, pharmaceutical preparations, animal tissue, etc.

As discussed below, exemplary embodiments are described with reference to silica as the sorbent, where the substance of interest is nucleic acids. Other sorbents could be used to isolate other materials of interest. By way of example only, the sorbent can contain polymers, carboxylic coatings, cyanopropyl, aminopropyl, poly(styrenedivinylbenzene), extractable petroleum hydrocarbons, alumina, magnesium silicate, diol, etc. Various functional groups or ionic materials, such as propylsulfonic acid groups (PRS) or metal (e.g., magnesium) ions can also be present in the sorbents, for example, to aid in separations. The sorbent can further be coated, for example with aminopropyl, primary/ secondary amine, quaternary ammonium, carboxylic or sulfonic groups, for instance. The sorbent can also be comprised of beads, which can be magnetic or paramagnetic, such as Oligo Magnetic Beads used, for example, in isolation of mRNA from cell lysates and tissues. Other examples of sorbent material include, but are not limited to, silica, acid washed silica, glass beads, acid washed glass beads, zeolite, silica gel, filters embedded with silica particles, or mixtures of the above.

A prior art SPE process 10 is depicted in FIG. 1. At step 12, the sample matrix is prepared. In traditional solid phase extraction using the QIAamp system, for example, the sample is limited to 140 µl, and larger samples will require multiple centrifugations. At step 14, the sample is added to a vial of lysis buffer and allowed to incubate for a period of 10 minutes. The lysis buffer breaks down cellular components in the sample to permit access to the compound of interest. For instance, in a DNA assay, the lysis buffer breaks down cell walls to gain access to the DNA located at the nucleus. An exemplary lysis buffer includes chaotropic salts and detergent which destabilize hydrogen bonds and proteins as well as mitigate hydrophobic interactions in the sample matrix. Further, the lysis buffer can help disrupt any tendency of the compound of interest to interact with water in a manner that might interfere with binding to the silica membrane, discussed further below. Some lysis buffers contain enzymes and/or solvents, and some buffers require the addition of heat for optimal performance. At step 16, ethanol is added to the sample in the lysis buffer, which is known to enhance the binding of nucleic acids and other compounds of interest to silica, discussed below. Next, at step 18, the sample mixed with lysis buffer and ethanol is processed through a column having a silica membrane to bind the compound of interest (e.g., nucleic acid) to the silica. This process involves two one-minute centrifugations. The lysate, which will contain impurities, proteins and other unwanted components of the sample matrix, is discarded. At step 20, wash buffers are placed into the silica column to remove unwanted materials from the silica membrane, such as residual proteins and salt. Two wash buffers are typically processed, each requiring a one-minute centrifugation. The first wash (Wash 1) can contain a small amount of chaotropic salt to remove any remaining proteins or colored contaminants from the membrane. A second wash (Wash 2) can contain a high concentration of ethanol to dissolve salts, which can interfere with isolation of the compound of interest and downstream testing. Wash 2 can be repeated if necessary. Following wash buffer removal, the column is centrifuged to so spin off residual ethanol at step 22 until the column is completely dried. Residual alcohol will interfere with elution, discussed below. At step 24, elution buffer is added to the silica column and allowed to incubate from one minute to rehydrate the compound bound to the silica. Different elution buffers are formulated for the compound of interest bound to the silica, for example elution buffers for DNA are slightly basic. The silica column is then centrifuged to separate the compound for downstream testing in a diagnostic instrument at step 26. Steps 24 and 26 can be repeated if desired. The process is now ended at step 30.

Figure 2:
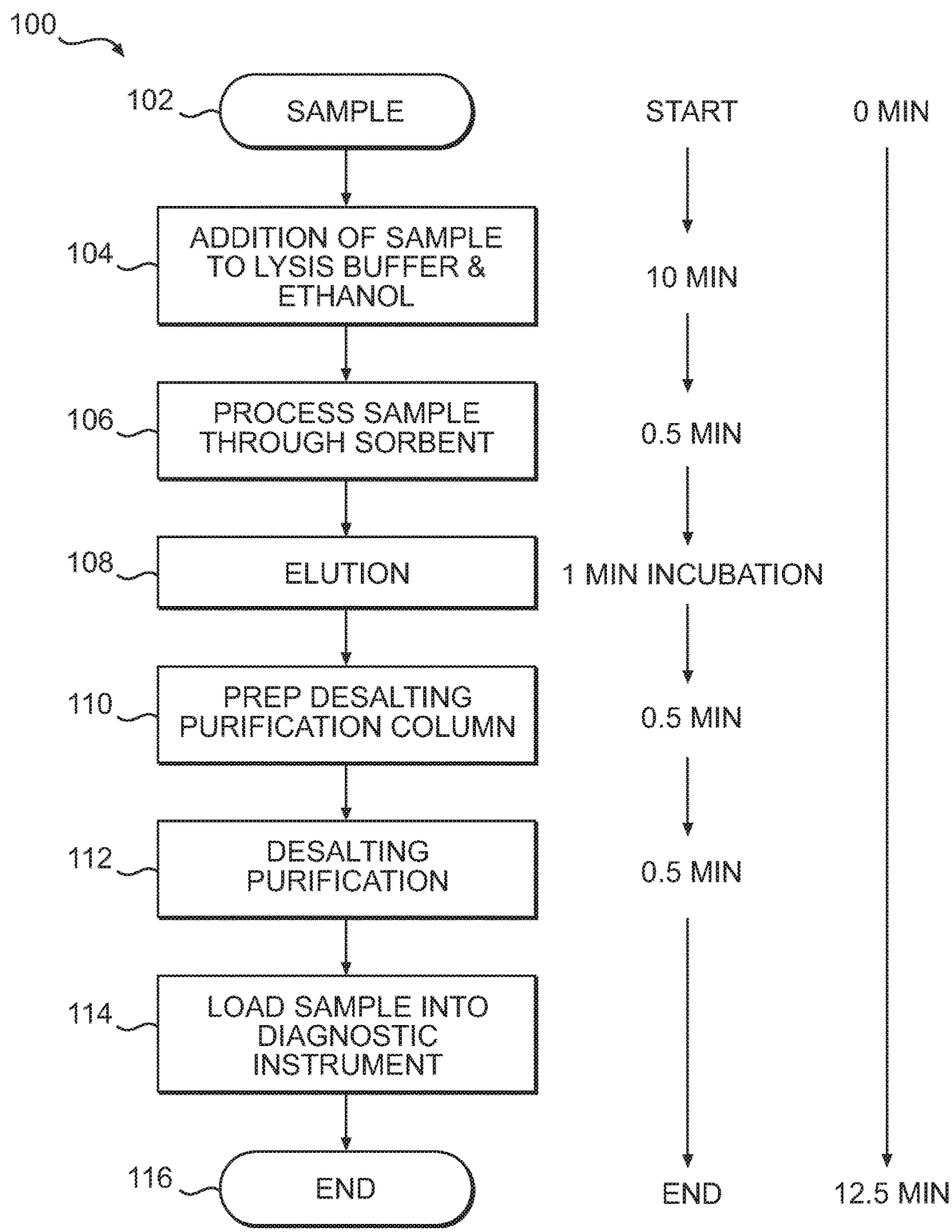
FIG. 2 illustrates an exemplary method for solid phase extraction of a compound of interest from a sample matrix according to the present disclosure.

Turning now to FIG. 2, an exemplary process is described according to the present disclosure. The process can be implemented using apparatus described with reference to FIG. 3, discussed herein below. At step 102, the sample matrix is prepared. Although in traditional solid phase extraction using the QIAamp system, for example, the sample is limited to 140 µl, the sample according to this exemplary process can be any size. At step 104, the sample is drawn into a syringe containing one or more buffers (the buffer can be premixed, can be a lysis buffer, can contain ethanol and can be added either sequentially or premixed) and allowed to incubate for a period of 10 minutes. At step 106, the sample mixed with lysis buffer and ethanol is pushed through a sorbent membrane, e.g. silica, in the syringe to bind the compound of interest to the sorbent, discarding the lysate. At step 108, elution buffer is drawn into the syringe containing the sorbent membrane and optionally allowed to incubate for one minute to rehydrate the compound of interest bound to the sorbent. A desalting column containing storage buffer, as described below, is optionally emptied and attached to the syringe tip. The elution buffer containing the compound of interest and any residual materials are urged under pressure through the desalting column, which removes any residual contaminants at step 112. The solution containing the compound of interest exiting the desalting column is used for downstream testing in a diagnostic instrument at step 114. The process is now ended at step 116.

The time periods disclosed above are exemplary, and can be varied as necessary to accommodate the particular compound, methodology and sample matrix involved. Such optimization would be understood by one of skill in the art as a normal and expected activity in sample extraction involved in molecular diagnostics.

Figure 3:
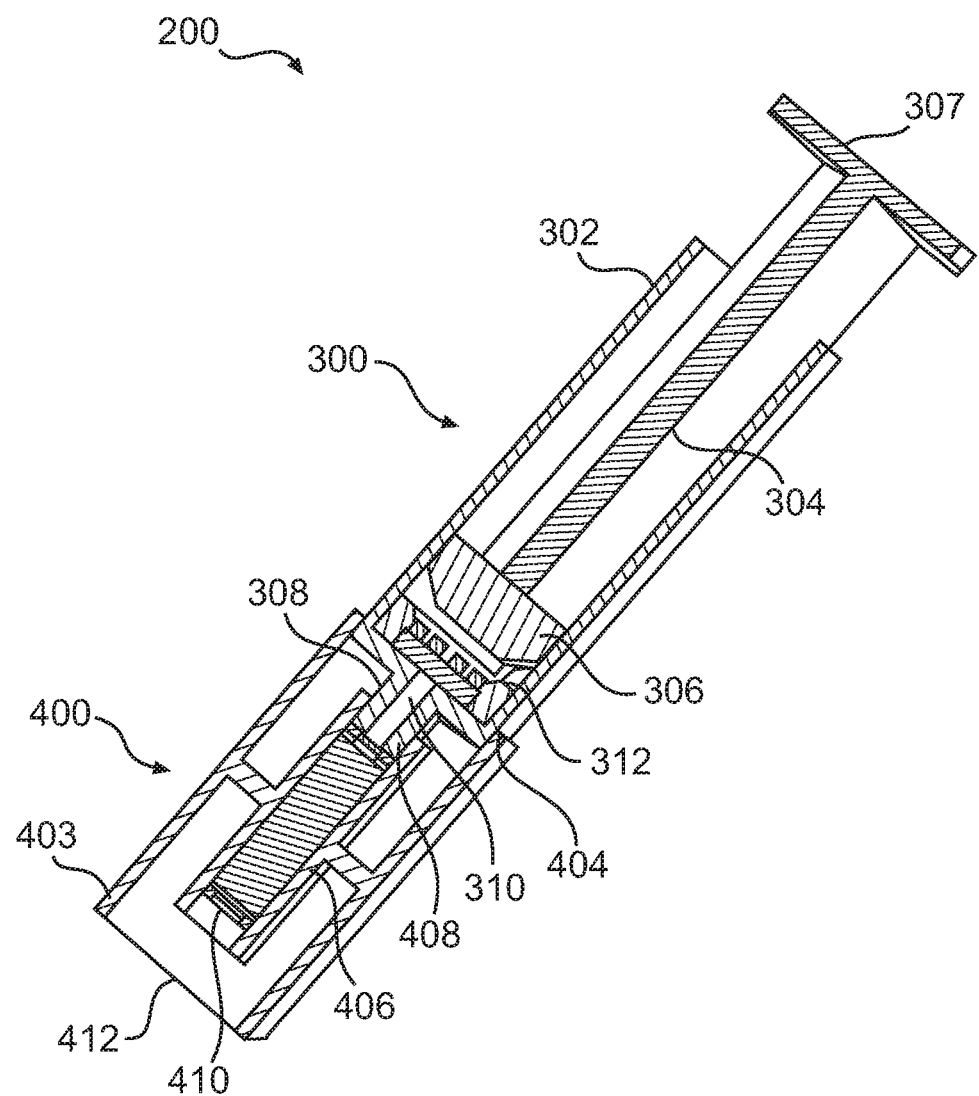
FIG. 3 depicts an exemplary system for performing the exemplary method depicted in FIG. 2.

Turning now to FIG. 3, an exemplary two-component system is depicted, which can be used in the performance of the exemplary method described above. The exemplary system provides a silica-based extraction in a syringe format that requires no centrifugation. Traditional silica-based extractions (such as QIAGEN QIAamp Viral RNA, catalog 52904) involve, as discussed above, loading a sample and/or buffers over a silica column and moving the sample/buffers through the column with repeated centrifugation steps, requiring a micropipette and a centrifuge.

Exemplary system 200 contains two major components. The first is syringe 300, comprising a barrel 302 and a plunger 304. The plunger 304 has a seal 306 attached thereto, and a plunger top 307 that in use is pushed or pulled to cause the seal to move in the barrel. The barrel can be in some embodiments translucent or transparent, and can also have indicia indicating internal volume gradations corresponding to seal position. At the opposite end of the barrel 302 from the plunger top 307 is hub 308 surrounding opening 310. The hub 308 can be in the form of an adapter or Luer taper. The syringe 300 contains a silica membrane 312 proximate to the hub 308 of the barrel 302.

The size of the syringe can vary. In exemplary embodiments, the syringe can be a 3 ml or a 5 ml syringe.

The second major component of the exemplary system 200 is a desalting purification column 400. The desalting purification column 400 comprises a barrel 403 with has a connector end 404 for attaching to the syringe 300. The connector end 404 can have an adapter or Luer taper. A desalting chamber 406 is packed with a material for removing salt and other residual impurities from a sample expelled through the desalting purification column following elution, as described above, which passes from first end 408 of the desalting chamber to second end 410 of the desalting chamber. In an illustrative embodiment, the material can include size exclusion chromatography media such as Sephadex, but other gel filtration or size exclusion chromatography media are available. The barrel 403 has an exit end 412, where desalted and purified sample exits. End 412 can be configured to mate with various containers, tubing, sample transport systems, etc., as desired.

Figure 4:
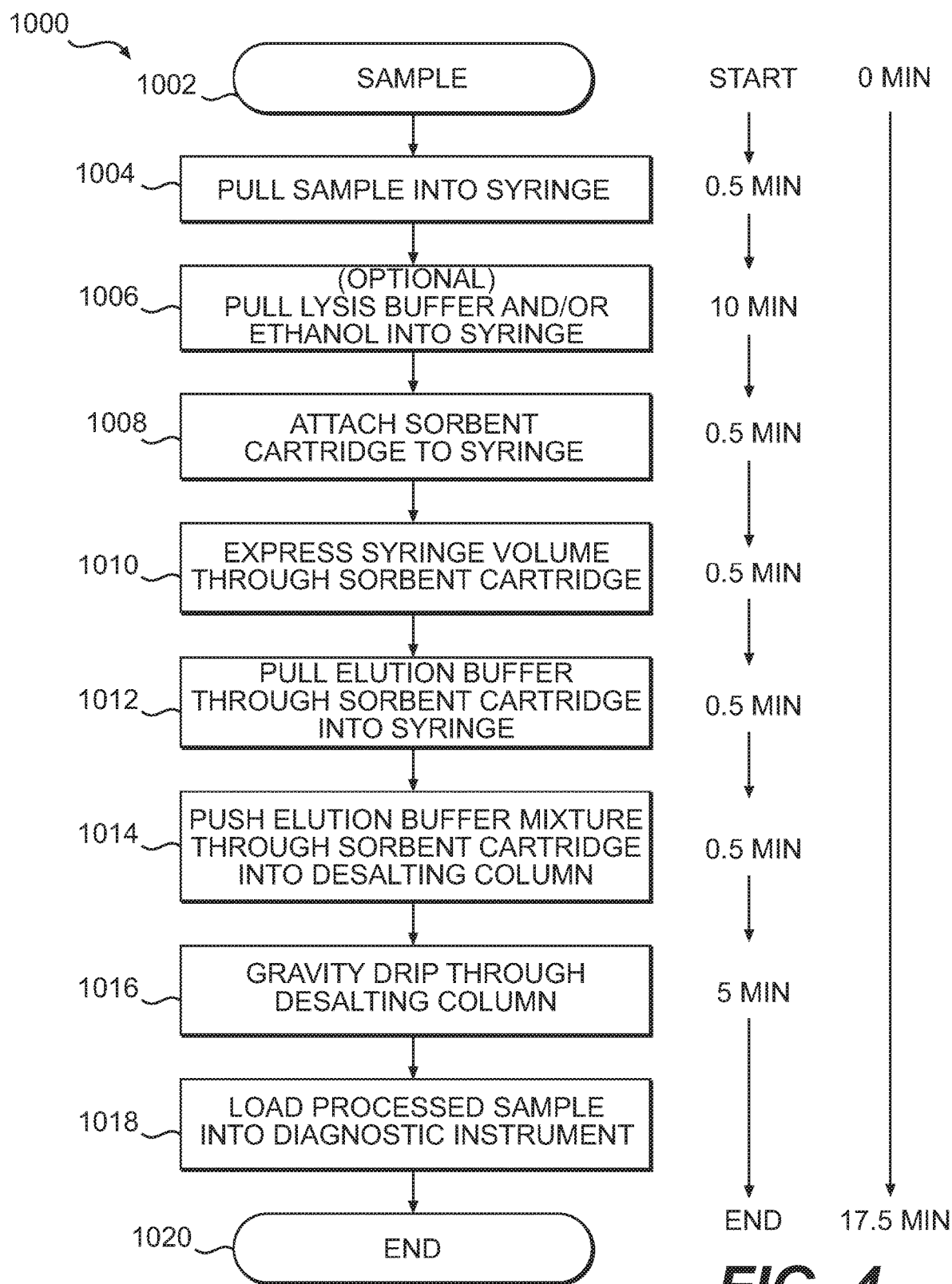
FIG. 4 illustrates another exemplary method for solid phase extraction of a compound of interest from a sample matrix according to the present disclosure.
Figure 5:
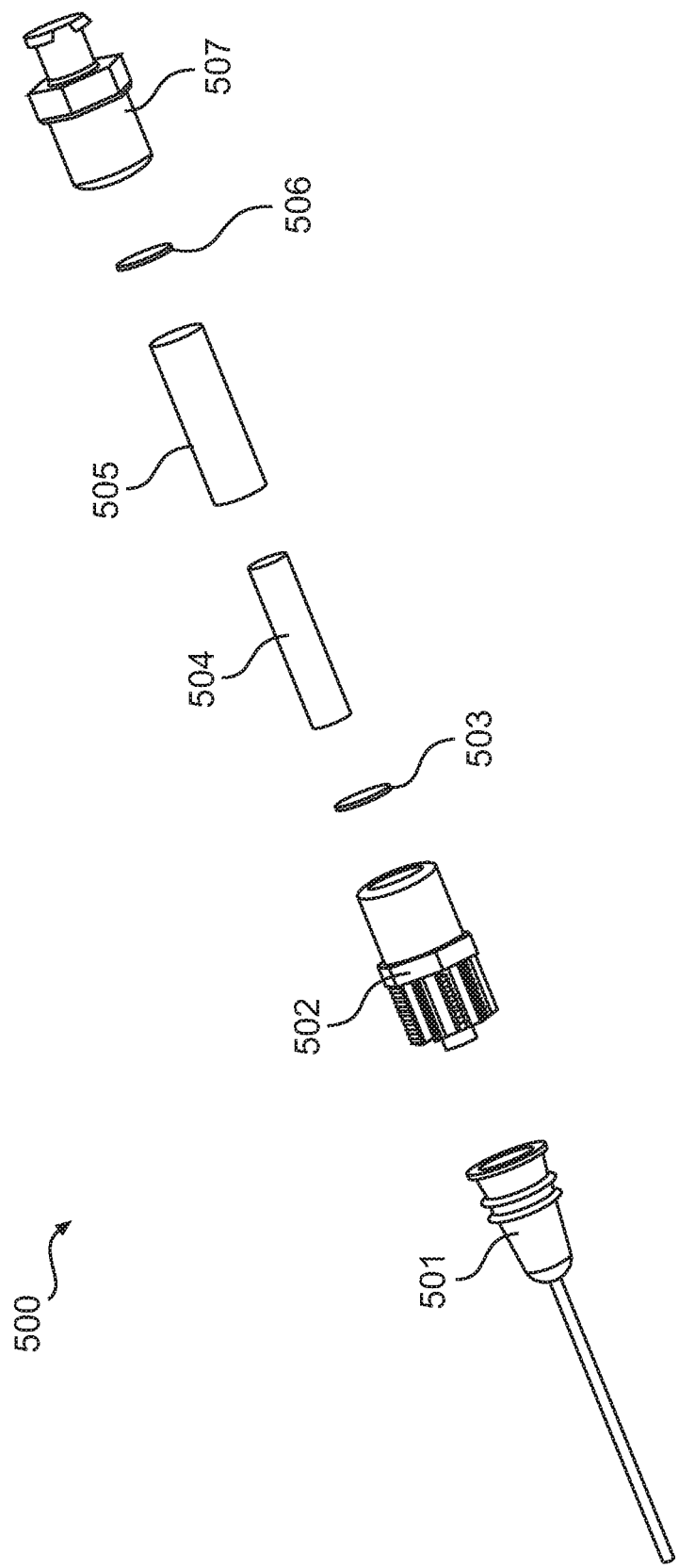
FIG. 5 depicts an exploded view of the exemplary sorbent cartridge for performing the exemplary method depicted in FIG. 4.
Figure 6:
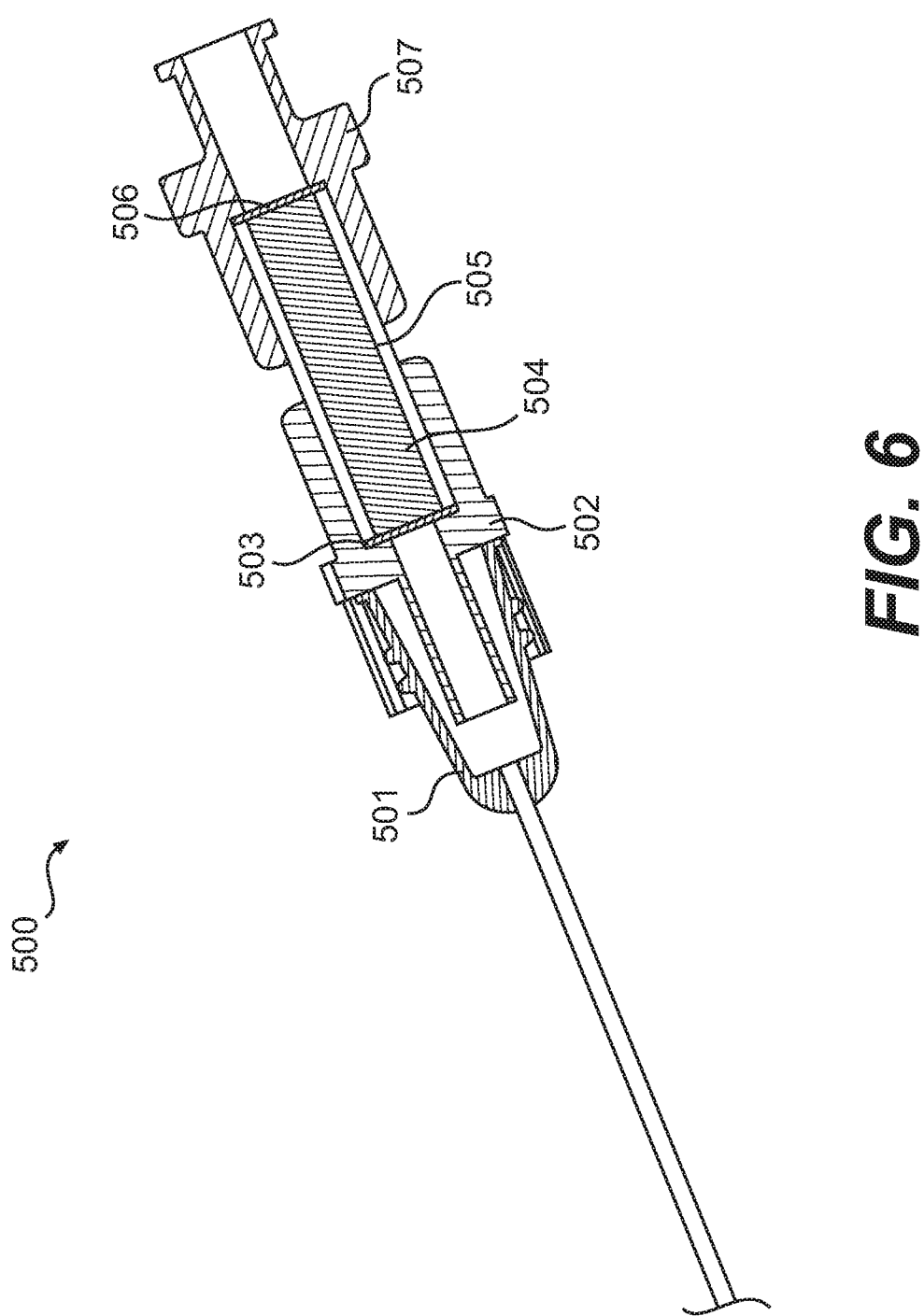
FIG. 6 depicts a cross section of the exemplary sorbent cartridge for performing the exemplary method depicted in FIG. 4.

Turning now to FIG. 4, an exemplary process is described according to the present disclosure. The process can be implemented using apparatus described with reference to FIG. 5, FIG. 6, and FIG. 7 discussed herein below. At step 1002, the sample matrix is prepared. Although in traditional solid phase extraction using the QIAamp system, for example, the sample is limited to 140 µl, the sample according to this exemplary process can be any size. At step 1004, the sample is drawn into a syringe. At step 1006, one or more buffers (the buffer can be premixed, can be a lysis buffer, can contain ethanol and can be added either sequentially or premixed) is drawn into a syringe and allowed to incubate for a period of 10 minutes. At step 1008, the sorbent cartridge depicted in FIG. 5 and FIG. 6 is attached to the syringe by a luer-lock fitting. At step 1010, the sample mixed with one or more buffers is pushed through the sorbent cartridge, which contains a sorbent, e.g. silica, to bind the compound of interest to the sorbent, discarding the lysate. At step 1012, elution buffer is drawn through the sorbent cartridge and into the syringe, to rehydrate the compound of interest bound to the sorbent. At step 1014, the elution buffer containing the compound of interest is pushed back through the sorbent cartridge and into the desalting column depicted in FIG. 7. The elution buffer containing the compound of interest and any residual materials are allowed to gravity drip through the desalting column, which removes any residual contaminants at step 1016. The solution containing the compound of interest exiting the desalting column is used for downstream testing in a diagnostic instrument at step 1018. The process is now ended at step 1020.

The time periods disclosed above are exemplary, and can be varied as necessary to accommodate the particular compound, methodology and sample matrix involved. Such optimization would be understood by one of skill in the art as a normal and expected activity in sample extraction involved in molecular diagnostics.

Figure 7:
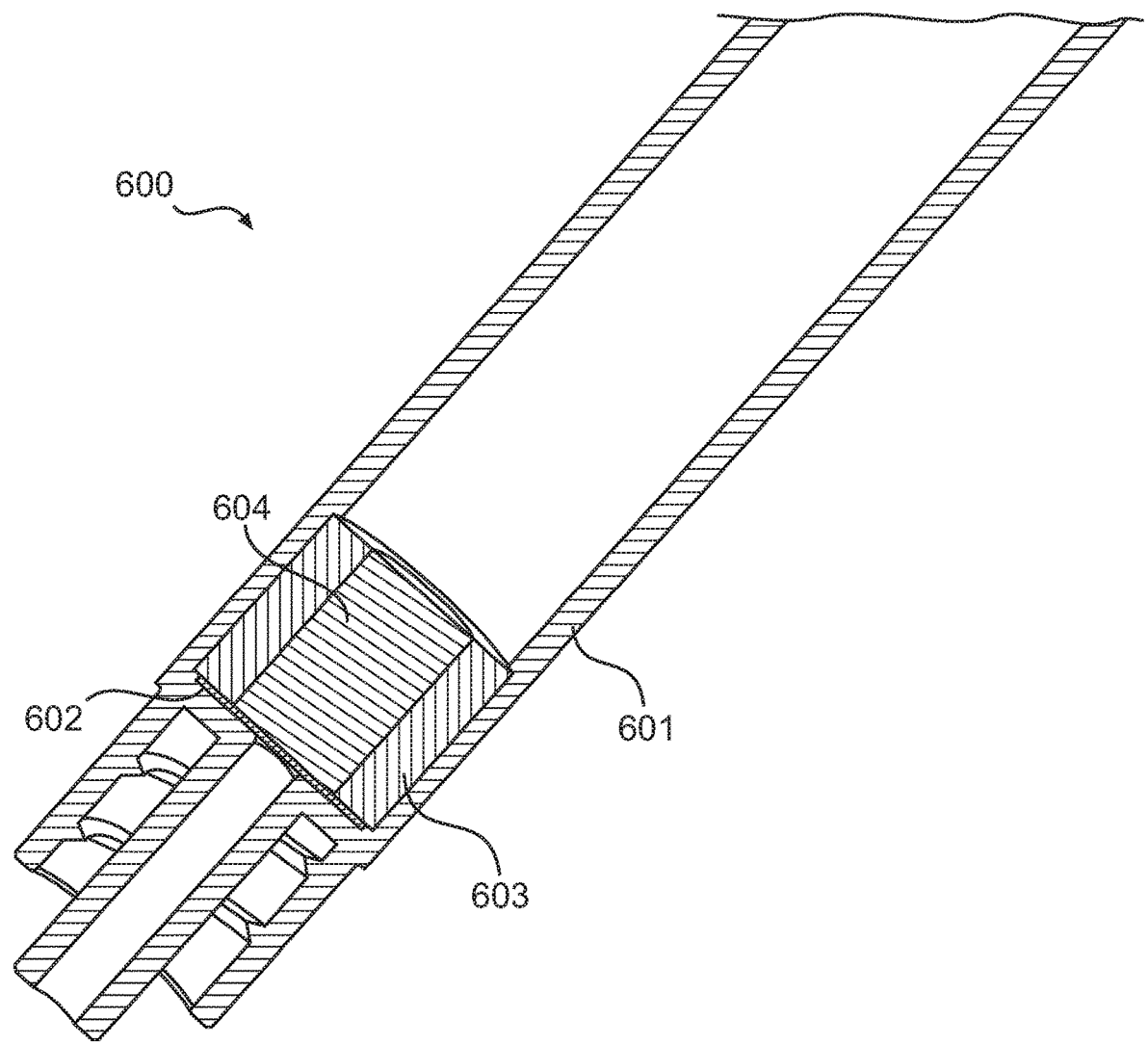
FIG. 7 depicts a cross section of the exemplary desalting column for performing the exemplary method depicted in FIG. 4.

Turning now to FIG. 5, FIG. 6, and FIG. 7, an exemplary system is depicted, which can be used in the performance of the exemplary method described above. The exemplary system provides a silica-based extraction in a syringe format that requires no centrifugation. Traditional silica-based extractions (such as QIAGEN QIAamp Viral RNA, catalog 52904) involve, as discussed above, loading a sample and/or buffers over a silica column and moving the sample/buffers through the column with repeated centrifugation steps, requiring a micropipette and a centrifuge.

Exemplary sorbent cartridge system 500 is depicted in FIG. 5 and FIG. 6. Sorbent cartridge 500 can be reversibly connected to a syringe (not depicted) by luer-lock fitting 507. The size of the syringe can vary. In exemplary embodiments, the syringe can be a 3 ml, 5 ml, or 10 ml syringe. Luer-lock needle 501 is connected to luer-lock fitting 502. Filter 503 fits into luer-lock fitting 502, and filter 506 fits into luer-lock fitting 507. Tubing 505 fits between luer-lock fitting 502 and luer-lock fitting 507. Sorbent material 504 is retained by the inner diameter of tubing 505, filter 503, and filter 506.

A further exemplary desalting column system 600 is depicted in FIG. 7. The desalting purification column 600 is based on syringe body 601. As depicted, filter 602 fits into the barrel of syringe body 601. Tubing 603 fits into the barrel of syringe 601, above filter 602. In an illustrative embodiment, gel filtration or size-exclusion chromatography media (e.g. Sephadex) 604 can be provided as shown within tubing 603 and is retained thereby. As depicted, the media 604 overlies filter 602. During shipping the syringe plunger (not depicted) is depressed and attached to the syringe body in order to retain gel filtration or size-exclusion chromatography media 604. During use, the elution buffer containing the compound of interest is placed above the gel filtration or size exclusion chromatography media 604. The elution buffer containing the compound of interest and any residual materials are allowed to gravity drip through the gel filtration or size exclusion chromatography media 604, which advantageously removes any residual contaminants.

In some embodiments, the syringe 300 can be pre-loaded with buffers, lysis buffers and/or ethanol. In other embodiments these materials can be stored separately. While not required, wash buffers can be drawn into the syringe to wash the silica membrane after the lysate is expelled in step 106 and before elution in step 108.

The exemplary systems disclosed herein may additionally comprise a prefilter for use with some sample matrices. These filters can be a part of the syringe at either the hub end or within the barrel, or fitted to the hub of the syringe using an adapter or Luer taper.

The exemplary syringe 300 of FIG. 3 uses a single plunger 304, but the system 200 can work with a dual- or multiple-plunger system, or a dual- or multiple-barrel syringe. Two syringes or barrels, each with a plunger that can deliver different buffers can be attached together into a joint housing. These syringes or barrels can either be separate from each other or set up in parallel or in series.

The plungers described in the illustrative syringe 300 is single; the plunger however could be a dual plunger with dual plunging capabilities. In an exemplary embodiment, an inner plunger to move one buffer through and then an outer plunger to move additional volumes through.

The exemplary system 200 is described to push and/or pull the sample and/or buffers through the process at various steps. At any step, the system could either gravity drip, push or pull, or any combination of push and pull motion can be used. In some exemplary embodiments, mechanical or electrical devices such as syringe pumps, linear actuators or vacuums can be employed.

While not depicted, a waste/buffer container could be utilized, for mating with either the syringe hub 308 or the exit end 412 of the desalting column 400. Such waste/buffer containers could be distributed in a series, or stacked for ease of use.

Buffers used with exemplary system 200 can be contained in buffer containers having hard casings or in blister packs. Buffer delivery can occur through gravity drip, pulling/pushing on the syringe and/or pierce able foil valves or directional ball check valves. The elution buffer as described above can in an illustrative embodiment be pre-aliquoted in single use tubes.

While the reaction is incubating in the syringe, the desalting purification column may optionally be prepared at step 110 by depressing a plunger (not shown) to remove a storage buffer. The desalting purification column is separated from the plunger and attached to the syringe 300. The plunger 304 is depressed, moving the sample from the syringe 300 to the desalting column 400 and ultimately out the exit end 412 for downstream processing.

Example 1

In an exemplary process, plasma is extracted from whole blood. In a still further exemplary embodiment, whole blood can be used as a sample matrix after being processed with a Rapid Plasma Dilution Buffer (RPDB). However, this system could work with other sample matrices such as, but not limited to serum, sputum and urine.

Whole blood was processed with equal parts RPDB and then glass-fiber filtered to obtain an artificial plasma material. 0.4 mL of this material, spiked with HIV virus-like particles (HIV VLP) was mixed with lysis buffer and ethanol (1:4:4) and pushed through the silica membrane, followed by elution using elution buffer (within the system depicted in FIG. 3). The control was a QIAGEN column (using the same buffers and methods; no wash buffers; elution buffer passed over the column two times). For both the invention and the control, the desalting/purification column was not included in the system but carried out in a centrifuge using a commercially available Sephadex column. The control and the test using the system were not performed in the same experiment but with the same reagents. The samples were analyzed using a real-time PCR assay on a T-COR 8 analytical measuring device available from Tetracore, Inc. of Rockville, Md. The cycle threshold (Ct) value for the QIAGEN control was 32.4 cycles, and the value for the illustrative embodiment of the current disclosure was 32.5 cycles.

Example 2

Whole blood was processed directly on a QIAamp column and an embodiment of the invention. Two replicates of the invention and control were performed. For the QIAamp column control, 90 uL of blood was added to 360 uL AVL lysis buffer and 360 uL ethanol and allowed to incubate for a period of 10 minutes. The sample and buffers were centrifuged through the QIAamp column and discarded, followed by centrifugation of 60 uL of elution buffer through the QIAamp column and collection of the eluent. For the QIAamp column, the desalting/purification step was carried out in a centrifuge using a commercially available Sephadex column. For the invention, 500 uL of blood was added to 2.5 mL AVL lysis buffer and 2.5 ml ethanol and allowed to incubate for a period of 10 minutes. The sample and buffers were pushed through the silica membrane, followed by elution using elution buffer (using the system depicted in FIG. 3). For the invention, the desalting/purification step was carried out using the gravity drip desalting column depicted in FIG. 7, and eluted in a final volume of 330 uL. Note that the experiments were performed such that the concentration ratios for both the control and the invention are equivalent (90 uL/60 uL vs. 500 uL/330 uL). Both processed samples were analyzed using an RNAseP real-time PCR assay on a T-COR 8 analytical measuring device available from Tetracore, Inc. of Rockville, Md. The results are shown in Table 1.

TABLE 1

Comparison of Invention and QIAamp system.

| Sample | Ct |
|---|---|
| Invention | 34.6 |
| Invention | 33.4 |
| QIAamp | 34.2 |
| QIAamp | 32.7 |

The methods and systems described herein may transform physical and/or or intangible items from one state to another.

The elements described and depicted herein, including in flow charts and block diagrams throughout the figures, imply logical boundaries between the elements. However, according to convention, the depicted elements and the functions thereof may be implemented simultaneously, in parallel or in series where appropriate. Thus, while the foregoing drawings and descriptions set forth functional aspects of the disclosed systems, no particular arrangement of these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. e.g., through automation. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method for extracting a compound of interest from a sample matrix, comprising the steps of:
   a. drawing a sample matrix into a syringe having a plunger;
   b. contacting the sample matrix with a sorbent to bind the compound of interest to the sorbent;
   c. drawing an elution buffer into the syringe containing the sorbent; and d. expressing the elution buffer containing the compound of interest through a desalting column subsequent to pushing the elution buffer containing the compound of interest through the sorbent.

2. The method of claim 1, further comprising the step of mixing the sample matrix with one or more buffers.

3. The method of claim 2, wherein the syringe is prefilled with one or more buffer solutions before the sample matrix is drawn into the syringe.

4. The method of claim 2, wherein at least one buffer solution is placed in the syringe before the sample matrix is drawn into the syringe.

5. The method of claim 2, wherein at least one buffer solution is placed in the syringe after the sample matrix is drawn into the syringe.

6. The method of claim 2, wherein said one or more buffers comprises a plurality of buffers.

7. The method of claim 6, wherein at least two of the plurality of buffers are placed into the syringe sequentially.

8. The method of claim 6, wherein at least two of the plurality of buffers are placed into the syringe premixed.

9. The method of claim 2, wherein at least one of the one or more buffers is a lysis buffer.

10. The method of claim 2, further comprising the step of allowing the sample matrix and the one or more buffers to incubate for a suitable period of time after the mixing.

11. The method of claim 2, wherein the sorbent comprises beads which float free in the syringe when mixed with the sample matrix.

12. The method of claim 2, wherein at least one of said one or more buffers comprises an alcohol.

13. The method of claim 12, wherein the alcohol comprises ethanol.

14. The method of claim 1, wherein the sorbent comprises at least one material selected from the group consisting of: silica, acid-washed silica, glass beads, acid-washed glass beads, zeolite, silica gel, filters embedded with silica particles, and mixtures thereof.

15. The method of claim 1, wherein the sorbent is in the form of a sorbent membrane.

16. The method of claim 1, wherein the expressing comprises pushing or pulling the elution buffer containing the compound of interest through the desalting column using the plunger.

17. The method of claim 1, further comprising allowing the elution buffer containing the compound of interest to gravity drip through the desalting column.

18. The method of claim 1, further comprising the step of washing the sorbent between steps (b) and (c).

19. The method of claim 1, wherein the desalting column further comprises gel filtration or size-exclusion chromatography media.

20. The method of claim 1, further comprising pushing the elution buffer containing the compound of interest through the sorbent and subsequently through the desalting column in a single push, the single push resulting in a desalted liquid containing the compound of interest being ejected from the desalting column.

* * * * *